(12) United States Patent
Davidson et al.

(10) Patent No.: US 6,740,031 B2
(45) Date of Patent: *May 25, 2004

(54) SPECULUM

(75) Inventors: Gale E. Davidson, Indianapolis, IN (US); Kathryn L. Hier, Indianapolis, IN (US)

(73) Assignee: Hier-Spec, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/349,429

(22) Filed: Jan. 22, 2003

(65) Prior Publication Data

US 2003/0114734 A1 Jun. 19, 2003

Related U.S. Application Data

(63) Continuation of application No. 09/720,499, filed on Dec. 27, 2000, now Pat. No. 6,527,710, which is a continuation of application No. PCT/US99/14838, filed on Jun. 30, 1999
(60) Provisional application No. 60/092,301, filed on Jul. 10, 1998.

(51) Int. Cl.[7] .................................................. A61B 1/32
(52) U.S. Cl. ....................................... 600/222; 600/219
(58) Field of Search ................................ 600/201, 210, 600/211, 216, 219, 220, 235, 222

(56) References Cited

U.S. PATENT DOCUMENTS

| 196,600 | A |   | 10/1877 | Shiland |         |
|---------|---|---|---------|---------|---------|
| 325,647 | A |   | 9/1885  | Bailey  |         |
| 430,350 | A |   | 6/1890  | McCully |         |
| 2,483,233 | A | * | 9/1949 | Price et al. | 600/205 |
| 3,332,414 | A |   | 7/1967 | Gasper  |         |
| 4,385,626 | A | * | 5/1983 | Danz    | 600/220 |
| 4,966,130 | A | * | 10/1990 | Montaldi | 600/222 |
| 5,007,409 | A | * | 4/1991 | Pope    | 600/203 |
| 6,432,048 | B1 | * | 8/2002 | Francois | 600/220 |
| 6,527,710 | B1 | * | 3/2003 | Davidson et al. | 600/222 |

FOREIGN PATENT DOCUMENTS

DK     59995 A    7/1942

* cited by examiner

Primary Examiner—Robert C. Eduardo
Assistant Examiner—David Comstock
(74) Attorney, Agent, or Firm—Woodard, Emhardt, Moriarty, McNett & Henry LLP

(57) ABSTRACT

A speculum (18) including a combined first speculum blade and handle portion (20), a combined second speculum blade and link portion (62), a speculum handle portion and a plurality of combined ribs and links (76). Each of the combined ribs and links (76) is movably coupled to the combined first speculum blade and handle portion (20) and to the combined second speculum blade and link portion (62) to movably couple the combined first speculum blade and handle portion (20) to the combined second speculum blade and link portion (62). The speculum handle portion (46) is movably coupled to the combined first speculum blade and handle portion (20) and to the combined second speculum blade and link portion (62) to actuate the combined first speculum blade and handle portion (20) and the combined second speculum blade and link portion (62) relative to each other between a first orientation (illustrated in FIG. 4) in which the speculum (18) is configured to be inserted into an incision, meatus or the like, and a second orientation (illustrated in FIG. 5) in which the speculum is configured to aid in examination, treatment or the like, of the incision meatus or the like.

18 Claims, 2 Drawing Sheets

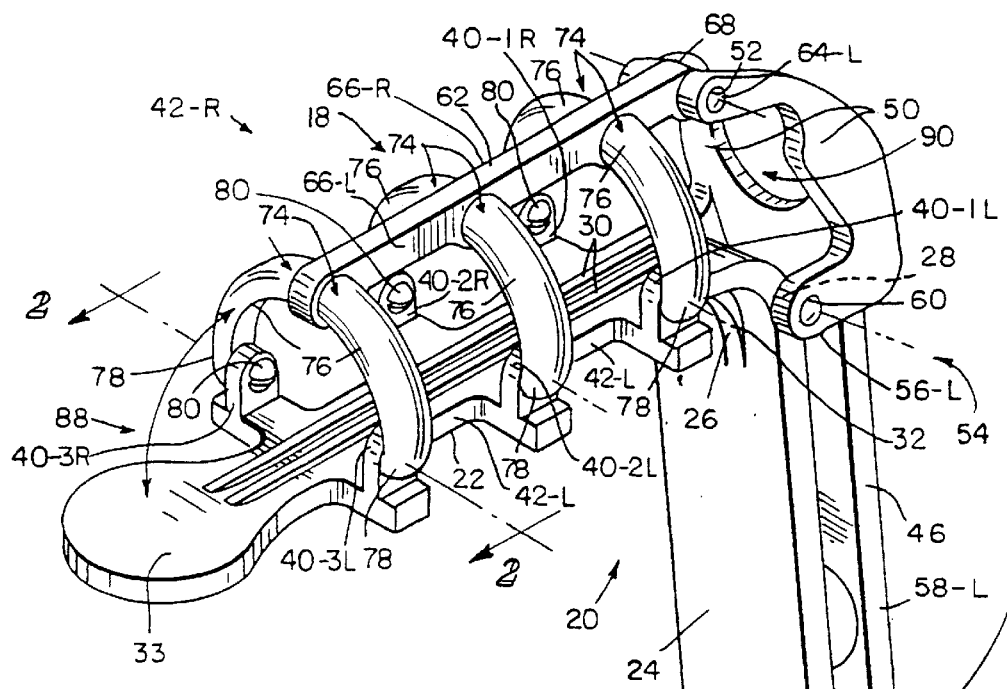
FIG. 1
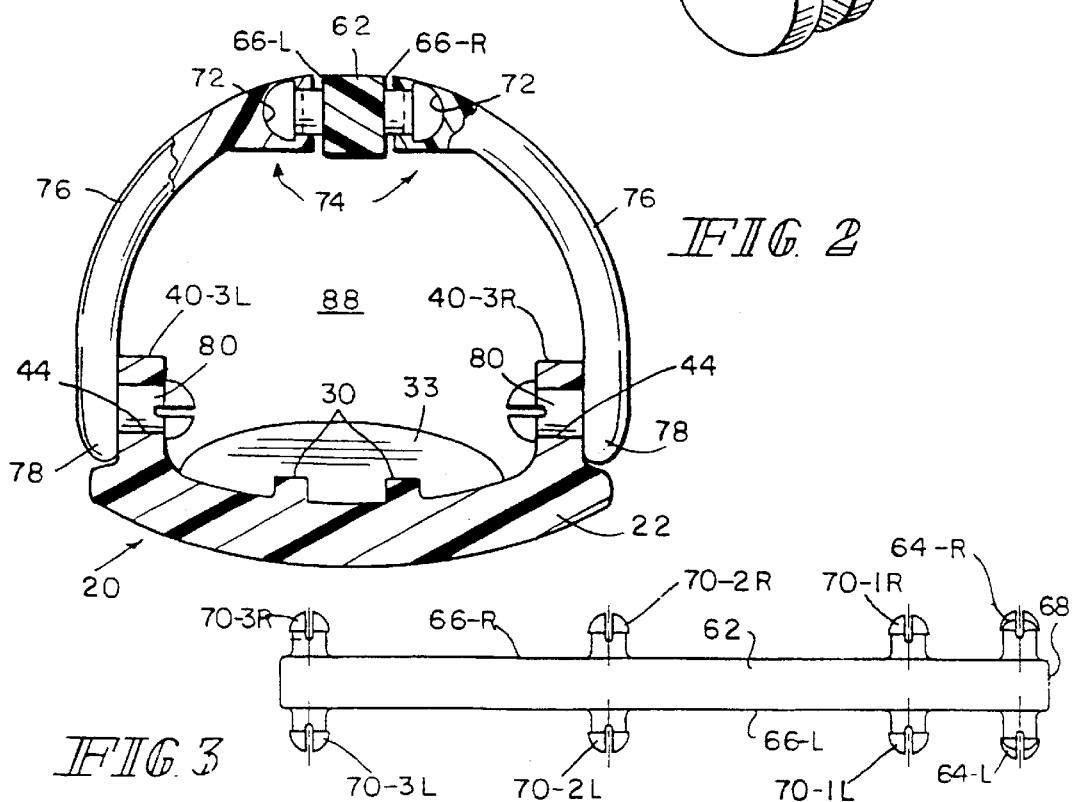
FIG. 2
FIG. 3

SPECULUM

CROSS-REFERENCE TO RELATED APPLICATIONS

The present application is a continuation of U.S. patent application Ser. No. 09/720,499 filed Dec. 27, 2000, now U.S. Pat. No. 6,527,710 which is a continuation of International Patent Application No. PCT/US99/14838 filed Jun. 30, 1990, which is continuation of U.S. Provisional Patent Application No. 60/092,301 filed Jul. 10, 1998, which is hereby incorporated by reference in its entirety.

FIELD OF THE INVENTION

This invention relates to specula. It is disclosed in the context of a gynecological speculum, but is believed to be useful in other applications as well.

BACKGROUND OF THE INVENTION

Several types of gynecological specula are known. The earlier types are designed and manufactured to be sterilizable. Many of the more recent types are resin or filled resin types, designed and manufactured to be disposable. Many of these later types are molded transparent or semitransparent plastic to assist in examination. Some employ optical waveguiding materials either integrally or as attachments, again to assist in examination. An illustrative, but by no means exhaustive listing of the various known types of specula includes the following U.S. Pat. Nos. 672,239; 1,150,749; 3,702,606; 3,890,961; 3,985,125, 4,206,750; 4,766,887; 4,884,559; 4,971,036; 5,052,372; 5,072,720; 5,179,937; 5,179,938; 5,458,595; and, 5,499,964. No representation is intended by this listing that the listed references constitute the only, or the closest, relevant art, or that no better references exist. Nor should any such representation be inferred.

DISCLOSURE OF THE INVENTION

A speculum includes a first member, a second member, a third member, and a plurality of fourth members. Each of the fourth members is movably coupled to the first member and to the second member to movably couple the first member to the second member. The third member is movably coupled to the first member and to the second member to actuate the first member and the second member relative to each other between a first orientation in which the speculum is configured to be inserted into an incision, meatus or the like, and a second orientation in which the speculum is configured to aid in examination, treatment or the like, of the incision, meatus or the like.

Illustratively according to the invention, the fourth members are provided in pairs.

Further illustratively according to the invention, each of the fourth members is pivotally coupled to the first member and to the second member.

Additionally illustratively according to the invention, the third member is pivotally coupled to the first member and to the second member.

BRIEF DESCRIPTION OF THE DRAWINGS

The invention may best be understood by referring to the following detailed description and accompanying drawings which illustrate the invention. In the drawings:

FIG. 1 illustrates a perspective view of a speculum constructed according to the invention in a use orientation;

FIG. 2 illustrates a sectional view of the speculum illustrated in FIG. 1, taken generally along section lines 2—2 of FIG. 1;

FIG. 3 illustrates a top plan view of a detail of the speculum illustrated in FIGS. 1–2;

DETAILED DESCRIPTION OF AN ILLUSTRATIVE EMBODIMENT

Figure 4:
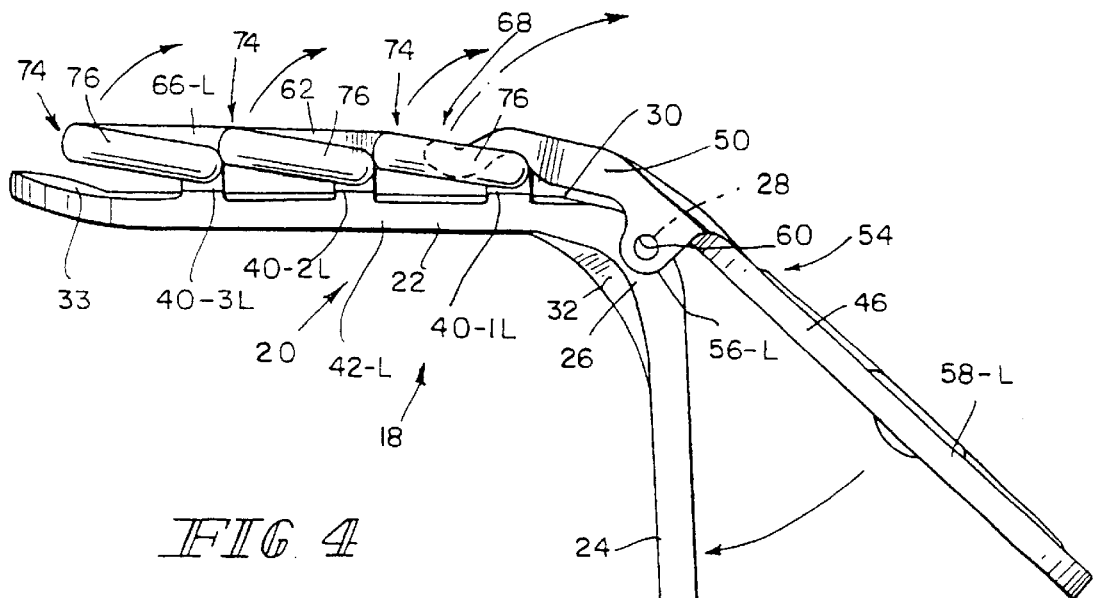
FIG. 4 illustrates a side elevational view of the speculum of FIG. 1 in an insertion orientation; and, FIG. 5 illustrates a side elevational view of the speculum of FIG. 1 in a use orientation.

The speculum of the invention may be constructed from any suitable material or combination of materials, such as filled and/or unfilled resin materials, illustratively to permit its components to be conveniently formed by, for example, injection molding and assembled by, for example, snapping them together. Additionally, if the materials are transparent or semitransparent, this can aid in examination conducted using the speculum. Additionally, if optical waveguiding materials and principles are employed in the design and construction of a speculum constructed according to the invention, this can further aid in examination conducted using the speculum.

Referring now to FIGS. 1–5, the speculum 18 includes a combined first speculum blade and handle portion 20. Portion 20 includes a region 22 generally defining a first speculum blade and a region 24 generally defining a first speculum handle portion. Regions 22, 24 are substantially smoothly integrated in region 26 into a single molded speculum portion 20. A transversely extending, through passageway 28 is formed on portion 20 in region 26. Ribs 30 and webs 32 are molded into portion 20 and extend between regions 22 and 24 through region 26 to strengthen portion 20. The forwardmost end 33 of blade region 22 illustratively includes a generally part circular curvature, perhaps best illustrated in FIG. 1, and a forwardly and upwardly concave curvature, perhaps best illustrated in FIGS. 4–5. Blade region 22 is also provided with a plurality, illustratively three, of pairs of ears 40-1L, 40-1R; 40-2L, 40-2R; and, 40-3L, 40-3R, one of each pair of which extend upwardly from respective opposite lateral edges 42-L and 42-R of blade region 22. Each ear 40-1L, 40-1R, 40-2L, 40-2R, 40-3L and 40-3R is provided with a transversely extending, through passageway 44, best illustrated in FIG. 2.

A speculum handle portion 46 includes at its upper end 48 a pair of upwardly extending drive arms 50, each having a transversely extending, through passageway 52. Downwardly from drive arms 50, toward a central region 54 of handle portion 46, a pair of pivotal mounting ears 56-L and 56-R extend forwardly from respective opposite lateral edges 58-L and 58-R of handle portion 46. Each mounting ear 56-L, 56-R is provided with a transversely extending, through passageway 60. Speculum handle portion 46 is pivotally mounted to portion 20 by one or more pivot pins inserted through aligned passageways 28, 60.

A combined second speculum blade and link portion 62 includes a pair of pivot pins 64-L and 64-R extending from its respective left and right lateral edges 66-L and 66-R adjacent a proximal end 68 of portion 62. Pivot pins 64-L and 64-R are received in respective passageways 52 of respective drive arms 50 to mount portion 62 pivotally from portion 46. Additionally, a plurality, illustratively three, of pairs of pivot pins, 70-1L, 70-1R; 70-2L, 70-2R; 70-3L; 70-3R, best illustrated in FIG. 3, extend from its respective left and right lateral edges 66-L, 66-R. Pivot pins 70-1L, 70-1R, 70-2L, 70-2R, 70-3L, 70-3R are pivotally received in pivotal mounting holes 72, best illustrated in FIG. 2, in first ends 74 of respective combined ribs and links 76. The second ends 78 of combined ribs and links 76 include pivot pins 80, best illustrated in FIG. 2, which are pivotally received in respective through passageways 44 on ears 40-1L, 40-1R, 40-2L, 40-2R, 40-3L and 40-3R of combined first speculum blade and handle portion 20 in the assembled speculum.

Figure 5:
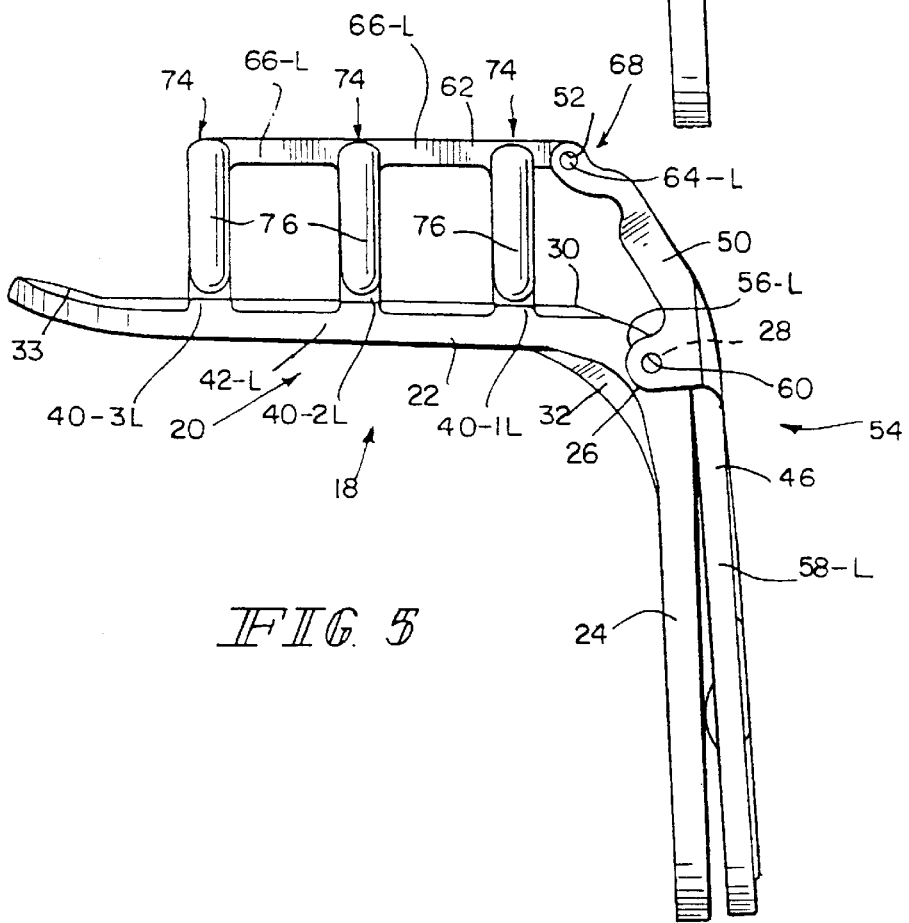

This arrangement mounts second speculum blade and link portion 62 to combined first speculum blade and handle portion 20 so that second speculum blade and link portion 62 can be selectively movably spaced from combined first speculum blade and handle portion 20, as best illustrated by comparing FIGS. 4 and 5, by varying the squeezing pressure between handle portion 46 and region 24 of combined first speculum blade and handle portion 20. In this way, the speculum 18 can be conveniently inserted into a meatus or incision with second speculum blade and link portion 62 collapsed into minimum spacing, illustrated in FIG. 4, from combined first speculum blade and handle portion 20. Then, once the speculum 18 is in position in the meatus or incision, squeezing pressure can be exerted between handle portion 46 and region 24 of combined first speculum blade and handle portion 20 to increase the spacing between second speculum blade and link portion 62 and combined first speculum blade and handle portion 20 to open the meatus or incision for observation and treatment. At the fully open position, with handle portion 46 and region 24 engaged, the speculum 18 can be so designed that the second speculum blade and link portion 62 is in an over-center orientation with respect to combined first speculum blade and handle portion 20, locking portions 20 and 62 in this orientation. This can best be appreciated with reference to FIGS. 1 and 5. Opening of the spacing between second speculum blade and link portion 62 and combined first speculum blade and handle portion 20 also provides a pathway 88 through the speculum 18 for the insertion into the meatus or incision of instruments for treatment. The space 90, best illustrated in FIG. 1, between drive arms 50 also promotes such insertion.

What is claimed is:

1. A speculum, comprising:
   a) a first speculum blade, wherein said first speculum blade has a first handle portion;
   b) second speculum blade;
   c) at least one link member mounted between said first speculum blade and said second speculum blade to allow said speculum to move from a compressed orientation to an open orientation; and,
   d) a second handle portion movably mounted to said first speculum blade and said second speculum blade, wherein movement of said second handle portion towards said first handle portion actuates movement of said speculum from said compressed orientation to said open orientation.

2. The speculum of claim 1 wherein said at least one link member is one of a plurality of rib members.

3. The speculum of said claim 2 wherein said open position places second speculum blade and said rib members in an over-centered orientation with respect to said first speculum blade such that said speculum is selectively locked in said open position.

4. The speculum of claim 2 wherein said second handle portion defines therein an instrument space aligned with a speculum passageway defined between said first speculum blade and said second speculum blade when said speculum is in said open orientation.

5. The speculum of claim 2 wherein said speculum is made from resin materials.

6. The speculum of claim 2 wherein said speculum is transparent or semi-transparent.

7. The speculum of claim 2 wherein is speculum is made from optical waveguiding materials.

8. The speculum of claim 2 wherein each of said first speculum blade and said second speculum blade include opposite first and second sides, and wherein said rib members are provided in opposing pairs, a first rib member of each pair extending between a first side of said first speculum blade and a first side of said second speculum blade and a second rib member of each pair extending between a second side of said first speculum blade and a second side of said second speculum blade.

9. The speculum of claim 2 wherein said first speculum blade further includes a forwardmost end with a generally part circular curvature.

10. The speculum of claim 9 where said forwardmost end further includes a forwardly and upwardly concave curvature.

11. A speculum, comprising:
    a) first speculum blade wherein said first speculum blade includes a first handle portion;
    b) a second speculum blade oriented substantially parallel to said first speculum blade;
    c) a plurality of link members extending between said first speculum blade and said second speculum blade, wherein said link members guide said first and second speculum blades in relative movement from a compressed orientation wherein said first and second speculum blades are substantially adjacent to an open orientation position wherein said first and second speculum blades are spaced apart; and,
    d) a second handle portion with an upper portion movably coupled to said second speculum blade, a central region movably coupled to said first speculum blade and a lower portion; and,
    e) wherein said lower portion of said second handle portion is movable towards said first handle portion to cause said speculum to move from said compressed orientation to said open orientation.

12. The speculum of claim 11 wherein said upper portion of said second handle portion defines a pair of drive arms, wherein said drive arms are pivotably coupled to said second speculum blade with at least one pivot pin.

13. The speculum of claim 11 wherein said central region of said second handle portion includes a pair of pivotal mounting ears extending from lateral edges of said second handle portion, and wherein said mounting ears of second handle portion are pivotably coupled to said first speculum blade.

14. The speculum of claim 11 wherein each of said plurality of link members includes at least one pivot pin portion, and wherein each said link member is pivotably coupled to one of said first speculum blade and said second speculum blade by said pivot pin portion received within a passageway in the respective one of said first speculum blade and said second speculum blade.

15. The speculum of claim 11 wherein one of said first speculum blade and said second speculum blade includes a plurality of pivot pin portions and wherein each of said plurality of link members includes at least one pivotal mounting hole and, wherein each of said plurality of link members is pivotably coupled to the respective one of said first speculum blade and said second speculum blade by one of said pivot pin portions received within said at least one pivotal mounting hole.

16. A method of using a speculum, comprising the steps of:
   a) providing a speculum having a first speculum blade wherein said first speculum blade includes a first handle portion, a second speculum blade, at least one link member extending between first speculum blade and said second speculum blade, and a second handle portion with an upper end portion coupled to said second speculum blade, a central region coupled to said first speculum blade and a lower end portion;
   b) rotating said lower end portion of said second handle portion to a spaced relationship from said first handle portion to place said speculum in a compressed orientation;
   c) inserting at least portions of said first and second speculum blades into a site for examination; and,
   d) applying squeezing pressure between said first handle portion and said lower end portion of said second handle portion to cause said first speculum blade and said second speculum blade to be movably spaced apart into a speculum open orientation.

17. The method of claim 16 comprising the step of inserting instruments for treatment into said site for examination through a pathway defined through said second handle portion and said speculum.

18. The method of claim 16 further comprising the step of selectively locking said speculum in said open orientation by movably spacing said second speculum blade and said at least one link member to an over-centered orientation relative to said first speculum blade.

* * * * *